United States Patent [19]

Stenberg

[11] 4,010,795
[45] Mar. 8, 1977

[54] COOLING UNIT
[75] Inventor: Kaj Stenberg, Staffanstorp, Sweden
[73] Assignee: Gambro AG, Zug, Switzerland
[22] Filed: Aug. 14, 1975
[21] Appl. No.: 604,880

Related U.S. Application Data
[63] Continuation of Ser. No. 484,341, June 28, 1974, abandoned.

[30] Foreign Application Priority Data
  Aug. 2, 1973  Sweden .............................. 7310636
[52] U.S. Cl. ............................... 165/46; 128/350 R
[51] Int. Cl.² ......................... F28F 7/00; A61F 7/00
[58] Field of Search ............... 128/350 R, 400, 402; 62/62, 530, 259; 126/204; 165/46

[56] References Cited
UNITED STATES PATENTS

| 1,622,903 | 3/1927 | Cox | 126/404 X |
|---|---|---|---|
| 2,504,142 | 4/1950 | Mingea | 165/46 |
| 2,512,990 | 6/1950 | Akerman | 165/46 X |
| 3,091,242 | 5/1963 | Johnson, Jr. et al. | 62/62 X |
| 3,169,528 | 2/1965 | Knox et al. | 128/350 R |
| 3,717,199 | 2/1973 | Dienst | 165/46 |
| 3,890,977 | 6/1975 | Wilson | 128/350 R |

FOREIGN PATENTS OR APPLICATIONS 17,621  9/1898  Switzerland .......................... 165/46

Primary Examiner—Charles J. Myhre
Assistant Examiner—Theophil W. Streule
Attorney, Agent, or Firm—Pierce, Scheffler & Parker

[57] ABSTRACT

A cooling unit especially adapted for cooling a living body organ comprises a readily formable coiled tubing for conducting a cooling medium, which tubing can be made to enclose the body object to be cooled, together with means for circulating a cooling medium through said tubing.

1 Claim, 3 Drawing Figures

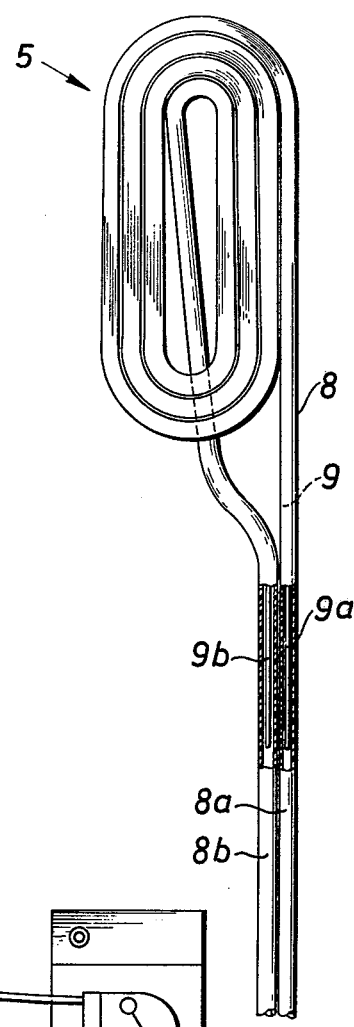
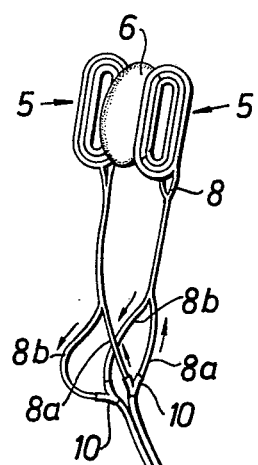
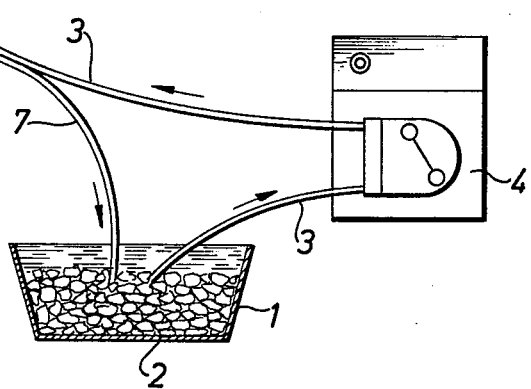
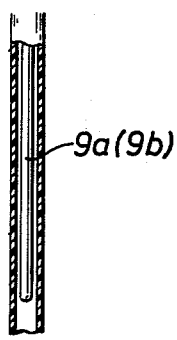

COOLING UNIT

This is a continuation of application Ser. No. 484,341 filed June 28, 1974, now abandoned.

The present invention involves a cooling unit including a source of cooling medium, for instance a container for ice-water, a tube for the transport of the cooling medium to at least one cooling body and a tube for removing the cooling medium used.

The cooling unit according to the invention is characterized by the fact that the said cooling body or cooling bodies consist of a formable coiled pipe, through which the cooling medium flows and which can be made to enclose tightly the object to be cooled.

The cooling unit according to the invention is especially adapted to cooling live body organs. Hence the invention also includes a method for cooling a live body organ with the aid of the unit defined above, for instance a kidney in vivo during a surgical operation. This method is characterized by the fact that the cooling bodies are made to enclose tightly the organ, while at the same time cooling liquid is pumped through them.

Though the cooling unit according to the invention is chiefly designed for medical use, it will seem obvious to those versed in the art that it may find other applications as well. In the following, however, only the surgical application will be described with reference to the accompanying drawings, which show a preferred embodiment of the object of the invention.

FIG. 1 shows diagrammatically a complete cooling unit according to the invention.

FIG. 2 shows on an enlarged scale a cooling body included in the cooling unit according to FIG. 1.

FIG. 3, finally, shows on a still larger scale a detail of FIG. 2.

As can be best seen in FIG. 1, the cooling unit shown by way of example includes a bowl or the like 1 containing a mixture of crushed ice and water. From this bowl 1 ice-water is led by means of a tube and a pump 4 to two cooling bodies 5 connected in parallel. The object 6 to be cooled is shown between these cooling bodies. This object might for instance be a kidney, on which the surgeon intends to perform an operation. In the drawing the cooling bodies 5 and the object 6 are shown spaced apart. In practice, however, the cooling bodies are formed in such a way, that they can be brought into close contact with the object 6. From the cooling bodies 5 the partially heated cooling water is led through a pipe 7 back to the bowl 1.

The construction of the cooling bodies 5 will be best seen in FIG. 2 and 3. The cooling body shown in these figures consist of a spirally or helically twisted hose 8 made of e.g. polyvinyl chloride. In order that this spirally twisted hose should permit a permanent deformation it includes a stiffening element 9, for instance in the form of a metal wire. As a suitable material for this metal wire may be chosen acidproof steel or another material both insensitive to water and harmless to tissues. The inlet of the cooling-body is indicated by 8a and its outlet by 8b. The metal wire 9 is of such length that its ends 9a and 9b extend into the inlet 8a and outlet 8b, respectively, of the hose. Hereby the cooling body 5 obtains a handle-like elongation, which facilitates its handling, when the cooling-body e.g. during a surgical operation has to be brought in under a partially exposed kidney. The numeral 10, finally, represents two branched connections used for the connection in parallel of the two cooling bodies 5.

The invention is of course not limited merely to the application described by way of example above, but may be modified within the scope of the following claims. Thus, an open system may be conceived in which the used cooling water is continuously discharged into a drain-pipe or the like. Of course other materials than the above mentioned may also be chosen. It is preferable, however, to choose such cheap materials that the whole of the cooling unit, or at least the cooling body or cooling bodies should be used only once, i.e. as non-recurring materials to be discarded immediately after being used, whereby the risk of contagion will be reduced for both the patient and the staff.

I claim:

1. In a cooling unit for use in cooling a live body organ, said cooling unit including a source of cooling medium; a cooling body; a first tube means for passage of cooling medium from said source to the cooling body, a second tube means for returning cooling medium from said cooling body to said source, and means for circulating cooling medium through said unit, the improvement wherein said cooling body consists essentially of a formable coil of cooling hose and a permanently deformable stiffening member in the form of a metal wire in said coil, said stiffening member being disposed entirely within the bore of the hose and occupying less than all of the cross-sectional space within the bore of the hose, which cooling body can be manually shaped to firm an enclosure about such body organ.

* * * * *